United States Patent [19]

Sims

[11] Patent Number: 4,943,162
[45] Date of Patent: Jul. 24, 1990

[54] ASTIGMATIC SELF-REFRACTOR AND METHOD OF USE

[76] Inventor: Clinton N. Sims, 3949 Evans Ave., Fort Myers, Fla. 33901

[21] Appl. No.: 310,334

[22] Filed: Feb. 13, 1989

Related U.S. Application Data

[63] Continuation-in-part of Ser. No. 116,322, Nov. 2, 1987, Pat. No. 4,840,479, which is a continuation-in-part of Ser. No. 23,980, Mar. 16, 1987, Pat. No. 4,820,040, which is a continuation of Ser. No. 670,398, Nov. 9, 1984, abandoned.

[51] Int. Cl.[5] .............................................. A61B 3/02
[52] U.S. Cl. .................................... 351/235; 351/234
[58] Field of Search ................ 351/233, 234, 235, 246

[56] References Cited

U.S. PATENT DOCUMENTS

| | | |
|---|---|---|
| 579,132 | 3/1897 | Clark . |
| 2,874,610 | 2/1959 | Wright . |
| 2,923,200 | 2/1960 | Wright . |
| 2,938,426 | 5/1960 | Armbruster et al. . |
| 2,968,213 | 1/1961 | Wright et al. . |
| 2,995,065 | 8/1961 | Wright et al. . |
| 3,015,988 | 1/1962 | Hemstreet . |
| 3,136,839 | 6/1964 | Safir . |
| 3,415,594 | 12/1968 | Aulhorn . |
| 3,428,398 | 2/1969 | Gottschalk . |
| 3,498,699 | 3/1970 | Wilkinson . |
| 3,524,702 | 8/1970 | Bellows et al. . |
| 3,572,908 | 3/1971 | Grolman . |
| 3,602,580 | 8/1971 | Samuels . |
| 3,664,631 | 5/1972 | Guyton . |
| 3,785,723 | 1/1974 | Guyton . |
| 3,791,719 | 2/1974 | Kratzer et al. . |
| 3,819,256 | 6/1974 | Bellows et al. . |
| 3,822,932 | 7/1974 | Humphrey . |
| 3,832,066 | 8/1974 | Cornsweet . |
| 3,841,760 | 10/1974 | Guyton . |
| 3,860,330 | 1/1975 | Persson . |
| 3,874,774 | 4/1975 | Humphrey . |
| 3,880,502 | 4/1975 | Humphrey . |
| 3,883,233 | 5/1975 | Guilino . |
| 3,969,020 | 7/1976 | Lynn et al. . |
| 4,021,102 | 5/1977 | Iizuka . |
| 4,105,302 | 8/1978 | Tate, Jr. . |
| 4,179,196 | 12/1979 | Persson et al. . |
| 4,180,323 | 12/1979 | Persson et al. . |
| 4,185,896 | 1/1980 | Buhler . |
| 4,190,332 | 2/1980 | Body et al. . |
| 4,215,919 | 8/1980 | Rybicki . |
| 4,385,813 | 5/1983 | Klein et al. ........................ 351/235 |
| 4,413,891 | 11/1983 | Rybicki ............................. 351/235 |
| 4,426,140 | 1/1984 | Stephens .......................... 351/204 |
| 4,436,390 | 3/1984 | Aoki ................................ 351/234 |
| 4,496,226 | 1/1985 | Augusto et al. .................... 351/234 |
| 4,523,822 | 6/1985 | Thurston .......................... 351/235 |
| 4,606,624 | 8/1986 | Wood .............................. 351/234 |

FOREIGN PATENT DOCUMENTS

598683  5/1960  Canada .
820766  9/1959  United Kingdom .

OTHER PUBLICATIONS

Alverez, "Development of Variable—Focus Lenses and a New Refractor", (1978).
Michaels, Visual Optics and Refraction (chapter 12) (1980).
Guyton, "Automated Clinical Refraction", (chapter 67 of Clinical Opthalmology (vol. 1), Duane, editor (1985).

(List continued on next page.)

*Primary Examiner*—Rodney B. Bovernick
*Attorney, Agent, or Firm*—Kilpatrick & Cody

[57] ABSTRACT

A new lens system and method of use for otherwise conventional refractors comprising a five-lens, variable crossed cylinder lens attachment and selectable fixed crossed cylinders which may be placed in the examining optical path. The variable crossed cylinder lens attachment includes two pairs of counter rotating cylinder lenses, each of which may be manipulated independent of the other, and a stationary sphere lens. The assembly also is connected to a computer so that the measurement of astigmatism may be made automatically. In addition, refractive techniques utilizing the disclosed crossed cylinder lens systems are described.

21 Claims, 4 Drawing Sheets

OTHER PUBLICATIONS

Kaufman, "Subjective Refraction: Fogging Use of the Astigmatic Dials", (chapter 39 of Clinical Ophthalmology (vol. 1), Duane, editor (1978).

Duke-Elder and Abrams, "Ophthalmic Optics in Refraction", (1970) pp. 438-439.

Egan, "A Resume of Crossed Cylinder Application and Theory".

Littmann, "Fundamental Considerations About Opthalmometry".

Wunsh, "The Crossed Cylinder", (chapter 38 of Clinical Ophthalmology (vol. 1), Duane, editor (1978).

"Dr. Thomson's 1985 Correspondence Course in Optics with Historical Commentary by Monroe J. Hirsch".

Friedman, "The Jackson Crossed Cylinder, a Critique", (1940).

Crisp, "A New Cross-Cylinder Test for Astigmatic Axis, Without Use of Test Type", (1942).

Stokes, "On a Mode of Measuring the Astigmatism of a Defective Eye", (1883).

Dennett, "The Stokes' Lens for Measuring Astigmatism", (1985).

Jackson, "A Trial Set of Small Lenses in a Modified Trial Frame", (1887).

ASTIGMATIC SELF-REFRACTOR AND METHOD OF USE

CROSS-REFERENCE TO RELATED APPLICATIONS

This application is a continuation-in-part of application Ser. No. 07/116,332 (now U.S. Pat. No. 4,840,479) filed Nov. 2, 1987, entitled "Crossed Cylinder Lenses Refractor with Three-lens Variable Crossed Cylinder Assembly and Method of Use," which application is a continuation-in-part of application Ser. No. 07/023,980 (now U.S. Pat. No. 4,820,040) Filed Mar. 16, 1987, entitled "Crossed Cylinder Lenses Refractor and Method of Use," which application is a continuation of application Ser. No. 06/670,398 filed Nov. 9, 1984 now abandoned, all of which applications are incorporated herein in their entirety by this reference.

FIELD OF THE INVENTION

This invention relates to subjective optical refractors used to determine the refractive errors in the eyes of humans.

BACKGROUND OF THE INVENTION

A refractor is a known ophthalmic instrument typically having batteries of trial lenses used to determine and remedy the refractive errors of a patient' eye. In modern refractors there are similar left and right batteries which include lens disks or cells containing lenses of spherical and cylindrical power, means for rotating the lens cells to place a lens or a combination of lenses before the eye under examination and a means for setting the axis of the cylinder lens. A modern refractor typically also includes a synchronized or non-synchronized Jackson crossed cylinder to be used as a check test for the neutralization of astigmatism (cylinder power and axis), as well as auxiliary lenses.

Techniques for refracting utilizing the Jackson crossed cylinder and the various spheres and cylinders of the refractor are well known. As refraction is presently practiced, the patient's refractive error is expressed in a sphere and a cylinder at a certain axis, which in reality represents the spherical equivalent plus the final crossed cylinder at a certain axis that is required to neutralize the patient's refractive error.

Present refractors are designated as having either positive or negative cylinders. Techniques of refracting have been designed to utilize the negative cylinders (negative theory of refracting). The negative theorem can be converted for the use of positive cylinders (positive theory of refracting) but is awkward. Similar techniques for retinoscopy have been developed mainly for positive cylinders. Both the negative and positive cylinders can be utilized in a manifest refraction when a meridional straddle is maintained. This final manifest refraction is the most accurate, as well as the most time consuming part of the refraction technique. It is the manifest refraction from which the final refraction is determined in cooperative patients, which probably comprise 95% of the average opthalmologist's and optometrist's refraction cases.

A well known problem for refractionists in performing the manifest refraction is maintaining a meridional balance throughout the manifest refraction. In the technique commonly performed with the conventional refractor, the refractionist is required to move one spherical lens and two cylindrical lenses in order to show the patient two images which are different by a minimum cylindrical correction.

However, a significant optical error is introduced by conventional refractors during refraction of patients having an astigmatic error in accordance with this technique. A 0.125D spherical equivalent jump of the images presented to the patient occurs when such refractors are used in the final manifest refraction by presenting successive cylinder lenses. This spherical equivalent jump occurs because cylinder lenses have a spherical component (equal to one-half of the cylindrical component of opposite sign), and conventional trial lenses are graded in 0.25 diopter increments. Thus, successive cylinder lenses change the resulting spherical component by 0.125 diopter, which means the exact meridional balance can be retained only with every other cylinder increment. The problem for the patient is that the two crossed cylinder images presented to him are different by a spherical equivalent of 0.125D, and produce an inequality in image shape, i.e. the circle of least confusion becomes oval. That is, if one crossed cylinder image is a circle, the other image is an oval with the angular orientation depending on the axis of the cylinder. The images are therefore dissimilar. (This visual comparison is obvious when a video camera, which is made astigmatic, is refracted. One image is in focus and the other is out of focus.) With the negative cylinder technique of refracting, accommodation is introduced every other time the cylinder power is changed, and with the positive cylinder technique of manifest refracting, a fog is introduced every other time the cylinder power is changed and accommodation may or may not be induced.

The refractionist can make the image comparisons for the patient equal or constant, that is comparing circles to circles or ovals to ovals by introducing a 0.125 D sphere auxiliary lens. However, this requires the refractionist to change five lenses (two auxiliary lenses, one spherical lens and two cylindrical lenses) in order to show the patient just two similar images of no spherical equivalent difference and of a circle of least confusion that is decreasing or increasing in size. Thus, a technique utilizing an auxiliary lens in this manner is impractical and confusing in practice.

The U.S. Pat. No. 4,385,813, to Klein, et al., teaches a computerized refractor using sphere and cylinder lenses and intended to solve the refractor manipulation problems presented by conventional refractors, but this approach is expensive and does not prevent the 0.125D spherical jump described above, although it could perhaps be adapted to accomplish that with different programming or different lenses.

Another problem that the refractionist has is the inability to maintain the same meridional balance while using the Jackson crossed cylinder in order to check the cylinder power. If a fog is produced, as with the positive cylinder phoropters, the refractionist may be inclined to prescribe too much against-the-rule astigmatism. Theoretically, it is also possible to prescribe too much with-the-rule astigmatism when negative cylinders are used with a Jackson crossed cylinder in an eye which has had a cycloplegic.

Refraction in accordance with conventional techniques is particularly difficult where the patient and refractionist do not speak the same language because of the difficulty of communicating, even through a translator, during the complex series of comparisons necessary in the conventional refraction.

Another problem the refractionist has is the inability of many patients, especially older ones, to respond to the use of astigmatic dials. The reason for this difficulty is obvious when one realizes that the theory of the astigmatic dial is based on the conoid of Sturm, which exists only in a thin lens system, whereas the eye is a complicated thick lens system.

An additional problem that the refractionist has is teaching a technician or student to refract, which takes many years of experience. Computerized objective/subjective refractors have reduced this obstacle; however their cost is high, their accuracy debatable, and it is questionable whether such refractors increase refraction efficiency.

The mechanics of moving the lens wheels of the phoropter is most confusing and difficult to teach technicians and ophthalmologists. It is very important to the refractionist to be able to maintain a meridional balance when he increases and/or decreases the cylinder powers while maintaining the proper spherical equivalent.

SUMMARY OF THE INVENTION

The above mentioned problems experienced by the patient and refractionist are avoided or solved by use, as is described in my previous applications Ser. Nos. 06/670,398, 07/023,980, and 07/116,322, of a synchronized variable crossed cylinder attachment for a refractor and/or a refractor using selectable crossed-cylinder lenses rather than the cylinder lenses conventionally used.

The synchronized variable crossed cylinder attachment or assembly disclosed in my previous applications Ser. Nos. 06/670,398 and 07/023,980 comprises two crossed cylinder lenses, or two cylinder lenses of equal power but opposite sign, mounted so as to be positionable in front of the viewing tube of the refractor. The lenses are rotatable in opposite directions at equal rates, and the resulting axis of the lens pair is synchronized to the axes of the crossed cylinder lenses in the cylinder lens discs of the refractor.

Additional advantages may be achieved by modification of this variable crossed cylinder assembly in accordance with my previous application Ser. No. 07/116,332 by using one stationary positive cylinder lens in the assembly with two equal-power, counter-rotating negative cylinder lenses, each having a negative power equal to one-half of the power of the positive lens. Alternatively, a negative stationary lens can be used with positive rotating lenses. The improvement enhances the accuracy of measurement of astigmatism by spreading the angular separation of the positions of the counter-rotating cylinders for a given cylinder power change as compared to my previously described structure.

Yet additional advantages may be obtained by modifying this variable crossed cylinder assembly in accordance with the present invention to use one stationary positive sphere lens in the assembly with two pairs of equal-power, counter-rotating negative cylinder lenses, each having a negative power equal to one-half of the power of the positive sphere lens, with the combined lens axis of one pair of cylinder lenses offset 45 degrees from the other. Alternatively, a negative stationary sphere lens can be used with positive rotating cylinder lenses. The improvement of the present invention further enhances the accuracy and ease of measurement of astigmatism as discussed above. Moreover, the present invention also may be connected to a computer so that the measurement of astigmatism may be made automatically based upon the final positions of the combined lens axes of the pairs of cylinder lenses.

As were the objectives of my inventions disclosed in my previous applications, it is also an object of the present invention to provide a simple solution to the problems of the refractionist and the patient described above, by providing a simple manual refractor that will eliminate unequal visual comparisons.

Another object of the present invention is to provide the refractionist a faster technique of varying the crossed cylinders while maintaining the same spherical equivalent. With the replacement of the conventional cylinders in a refractor with the crossed cylinders, not only is the 0.125D image jump eliminated, but the refractionist is also able to maintain a perfect meridional straddle by changing only one lens (crossed cylinder) instead of three lenses (the auxiliary lens, the sphere lens and the cylinder lens) per change of the refraction crossed cylinder while maintaining the same spherical equivalent meridional balance.

An advantage of the invention is that practice of the two theorems of refracting (positive and negative cylinders) become the same when a perfect meridional balance is maintained after a spherical equivalent is determined.

A further advantage of the crossed cylinder lens system of the present invention is to allow the patient to view several hundred crossed cylinder powers at different angles in a matter of only a few seconds. If astigmatism is detected, it may then be confirmed with the selectable crossed cylinder lenses in the refractor at the determined axis.

Another advantage of the present invention is that the technique of fogging is faster, as well as mechanically easier, with the use of the selectable crossed cylinder lenses and/or the variable crossed cylinder lens assembly disclosed.

An additional advantage of the present invention is the elimination of the iatrogenic induction of with-the-rule or against-the-rule astigmatism inherent with the Jackson crossed cylinder refraction technique when a perfect meridional balance is not maintained as in previous techniques. The variable crossed cylinder assembly of the present invention can be used with the Jackson crossed cylinder, while the selectable crossed cylinder lens system disclosed will maintain a perfect meridional straddle.

A further advantage of the variable crossed cylinder lens assembly of the present invention is the replacement of the error-prone, audio-visual responses that are required with conventional refractors with a silent visual response.

Another advantage of the present invention is that the variable crossed cylinder lens assembly allows the refractionist to detect and neutralize any pre-refraction astigmatism many times faster than is presently possible as well as post-check the final astigmatic results.

An additional advantage of the present invention is that each pair of cylinder lenses may be varied independent of the other.

Another advantage of the present invention is that the patient may perform the astigmatic refraction himself merely by varying the positions of one or both of the pairs of cylinder lenses.

An additional advantage of the present invention is that the variable crossed cylinder lens assembly may be used as the ocular of a microscope, telescope, or video camera to neutralize any astigmatism present in the eye of the user and allow a clearer image to be presented.

Yet another advantage of the present invention is that measurement of astigmatism may be made automatically based upon the final positions of the combined lens axes of the pairs of cylinder lenses through the use of a computer connected to the variable crossed cylinder lens assembly.

Other advantages to the refractionist are:

The use of cycloplegics is rarely required, even for the young patient.

Objective refractors are not required to obtain an initial beginning point for the manifest refraction.

Retinoscopy is rarely required to perform an endpoint manifest refraction.

The time required to perform a manifest refraction for pathological or non-pathological patients is very significantly decreased.

The accuracy of refraction is significantly improved, thus reducing the optical remake rate.

Other objects, features and advantages of the present invention will become apparent with reference to the remainder of the specification, claims and drawings.

DETAILED DESCRIPTION OF THE DRAWINGS

Figure 1:
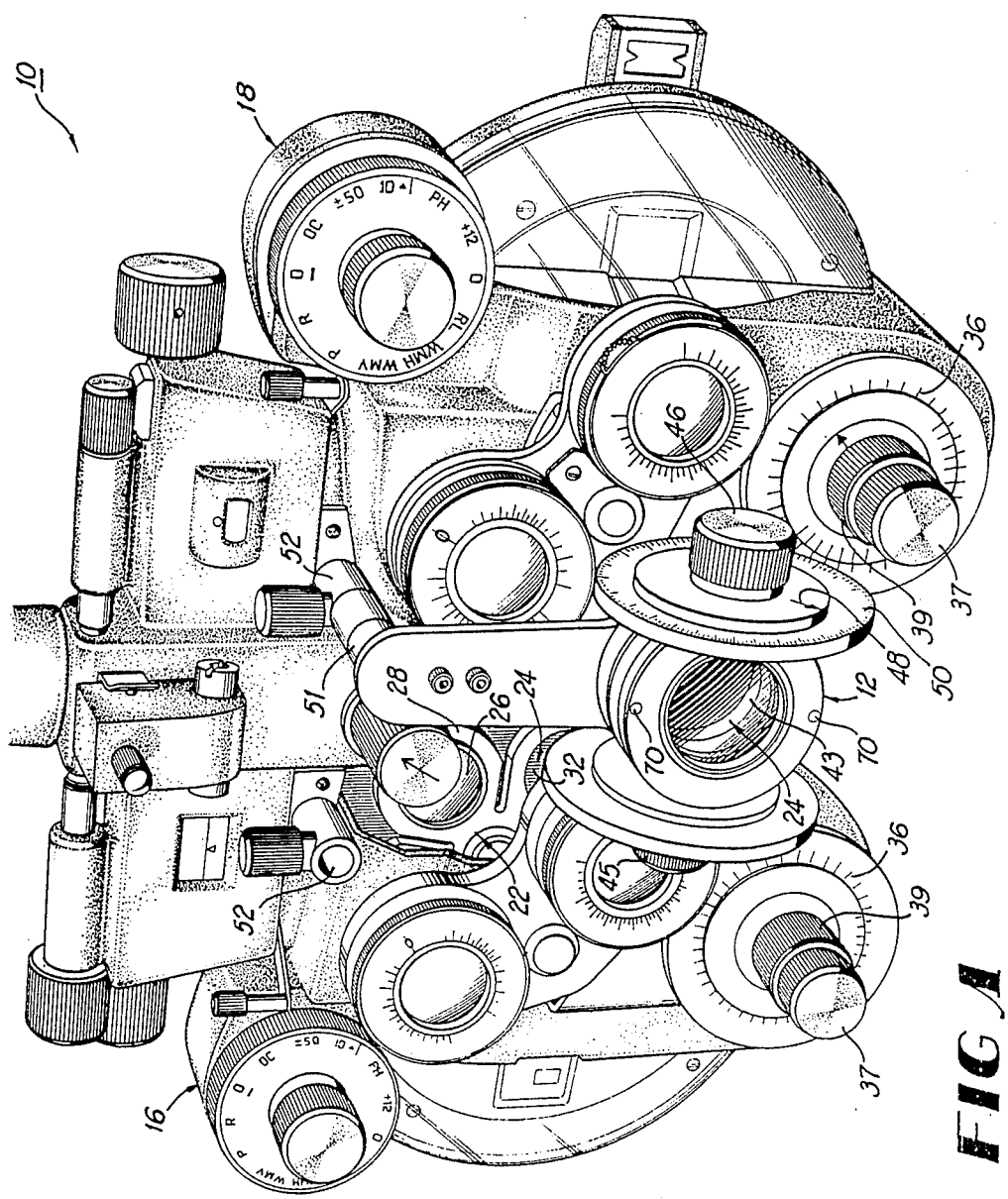
FIG. 1 is a perspective view of a substantially conventional refractor taken from the practitioner's side of the instrument showing the variable crossed cylinder lens assembly of the present invention mounted to the refractor and aligned with the viewing tube of the (patient's) left eye battery and showing the (patient's) right eye battery partly in elevation and partially broken away to reveal the forward crossed cylinder lens disk.

Referring to FIG. 1, the refractor 10 may include a right eye battery 16 and a left eye battery 18, and these batteries may be essentially mirror images. Refractor 10 need only include one battery, however, as only one eye need be refracted at a time. FIG. 1 shows the variable crossed cylinder lens assembly 12 of the present invention mounted on the refractor 10 so that its lenses are aligned with the viewing tube 24 of left eye battery 18. The right eye battery 16 is partially broken away to show the selectable crossed cylinder lens system 22 of the present invention, which is also identified on FIG. 2. Only the variable crossed cylinder lens assembly 12 and the selectable crossed cylinder lens system 22 of the present invention as incorporated in an otherwise conventional refractor 10 will be discussed. FIG. 1 shows the refractor 10 from the refractionist's side, and this side will be referred to as the front side of the instrument.

The major component parts of each battery 16 and 18 (FIGS. 1 and 2) include a sphere lens assembly 20, a selectable crossed cylinder lens assembly 22 and a variable crossed cylinder attachment 12. The patient positions his head to the rear of the instrument so that each of his eyes is in alignment with the viewing tubes 24.

SELECTABLE CROSSED CYLINDER LENS ASSEMBLY

The selectable crossed cylinder lens assembly 22 may comprise crossed cylinder lenses 26 and 27 mounted in a cylinder lens assembly of the type disclosed in U.S. Pat. No. 3,498,699, which patent is incorporated herein by reference in its entirety. It thus includes a pair of crossed cylinder lens discs 28 and 30 shown in FIG. 2. The forward disc 28 carries weak crossed cylinder lenses 26 and the rear disc 30 carries the strong crossed cylinder lenses 27.

The strong and weak crossed cylinder discs 28 and 30 carry sets of strong and weak crossed cylinder lenses of various powers mounted circumferentially on the discs, so that a selected lens will, upon rotation of the discs, come into alignment with the viewing tube 24. Each disc 28 and 30 carries four lenses and has one open position 32 which is aligned with the viewing tube 24 when no crossed cylinder lens within such disc 28 or 30 is desired.

The crossed cylinder (X/CYL) lens powers utilized in the preferred embodiment are as follows:

| WEAK X/CYL LENSES MOUNTED IN WEAK DISC 28 | STRONG X/CYL LENSES MOUNTED IN STRONG DISC 30 |
| --- | --- |
| ±0.125 D | ±0.625 D |
| ±0.25 D | ±1.25 D |
| ±0.375 D | ±1.875 D |
| ±0.50 D | ±2.50 D |

The power of the combination of the weak and strong crossed cylinders 26 and 27 seen through the viewing tube 24 may be presented in a display which indicates the total crossed cylinder lens power as seen through the viewing tube. For a positive crossed cylinder refractor, the orientation of the plus axis of the weak and strong crossed cylinders 26 and 27 as seen through the viewing tube 24 will be indicated on to the crossed cylinder axis scale 36. The designation of the positive or negative crossed cylinder refractor as seen in the display may include the total crossed cylinder sphere power followed by the total cylinder cylindrical power. For a positive crossed cylinder refractor, the sphere power value should be red and the cylindrical power value black in the display. For a negative crossed cylinder refractor, the sphere power value in the display should be black and the cylinder power value red because, by convention, black designates positive cylinder lenses and red negative cylinder lenses.

A suitable structure for accomplishing the desired objective of mounting crossed cylinder lenses 26 and 27 so that they may be selectively positioned in line with viewing tube 24 and may be rotated is disclosed in U.S. Pat. No. 3,498,699, mentioned above, particularly at columns 5 and 6.

As will be readily appreciated, the described arrangement permits the refractionist to control not only the total power of the crossed cylinder lenses 26 and 27 in alignment with the viewing tube 24 (by means of crossed cylinder power knob 37), but also the orientation of the axis of these lenses 26 and 27 (by means of cylinder axis rotation knob 39).

The described selectable crossed cylinder lens assembly makes possible the following crossed cylinder powers:

| WEAK X-CYL LENS IN WEAK DISC 28 | STRONG X-CYL LENS IN STRONG DISC 30 | DISPLAY X-CYL** (expressed in sphere plus cylinder notation) |
|---|---|---|
| 0.00 | 0.00 | 0.00 |
| ±0.125 | 0.00 | 0.12/0.25 |
| ±0.25 | 0.00 | 0.25/0.50 |
| ±0.375 | 0.00 | 0.37/0.75 |
| ±0.50 | 0.00 | 0.50/1.00 |
| 0.00 | ±0.625 | 0.62/1.25 |
| ±0.125 | ±0.625 | 0.75/1.50 |
| ±0.25 | ±0.625 | 0.87/1.75 |
| ±0.375 | ±0.625 | 1.00/2.00 |
| ±0.50 | ±0.625 | 1.12/2.25 |
| 0.00 | ±1.25 | 1.25/2.50 |
| ±0.125 | ±1.25 | 1.37/2.75 |
| ±0.25 | ±1.25 | 1.50/3.00 |
| ±0.375 | ±1.25 | 1.62/3.25 |
| ±0.50 | ±1.25 | 1.75/3.50 |
| 0.00 | ±1.875 | 1.87/3.75 |
| ±0.125 | ±1.875 | 2.00/4.00 |
| ±0.25 | ±1.875 | 2.12/4.25 |
| ±0.375 | ±1.875 | 2.25/4.50 |
| ±0.50 | ±1.875 | 2.37/4.75 |
| 0.00 | ±2.50 | 2.50/5.00 |
| ±0.125 | ±2.50 | 2.62/5.25 |
| ±0.25 | ±2.50 | 2.75/5.50 |
| ±0.375 | ±2.50 | 2.87/5.75 |
| ±0.50 | ±2.50 | 3.00/6.00 |

**For a + crossed cylinder refractor 0.12/0.25 is displayed as: 0.12 red 0.25 black
For a − crossed cylinder refractor 0.12/0.25 is displayed as: 0.12 black 0.25 red

VARIABLE CROSSED CYLINDER LENS ASSEMBLY

Figure 2:
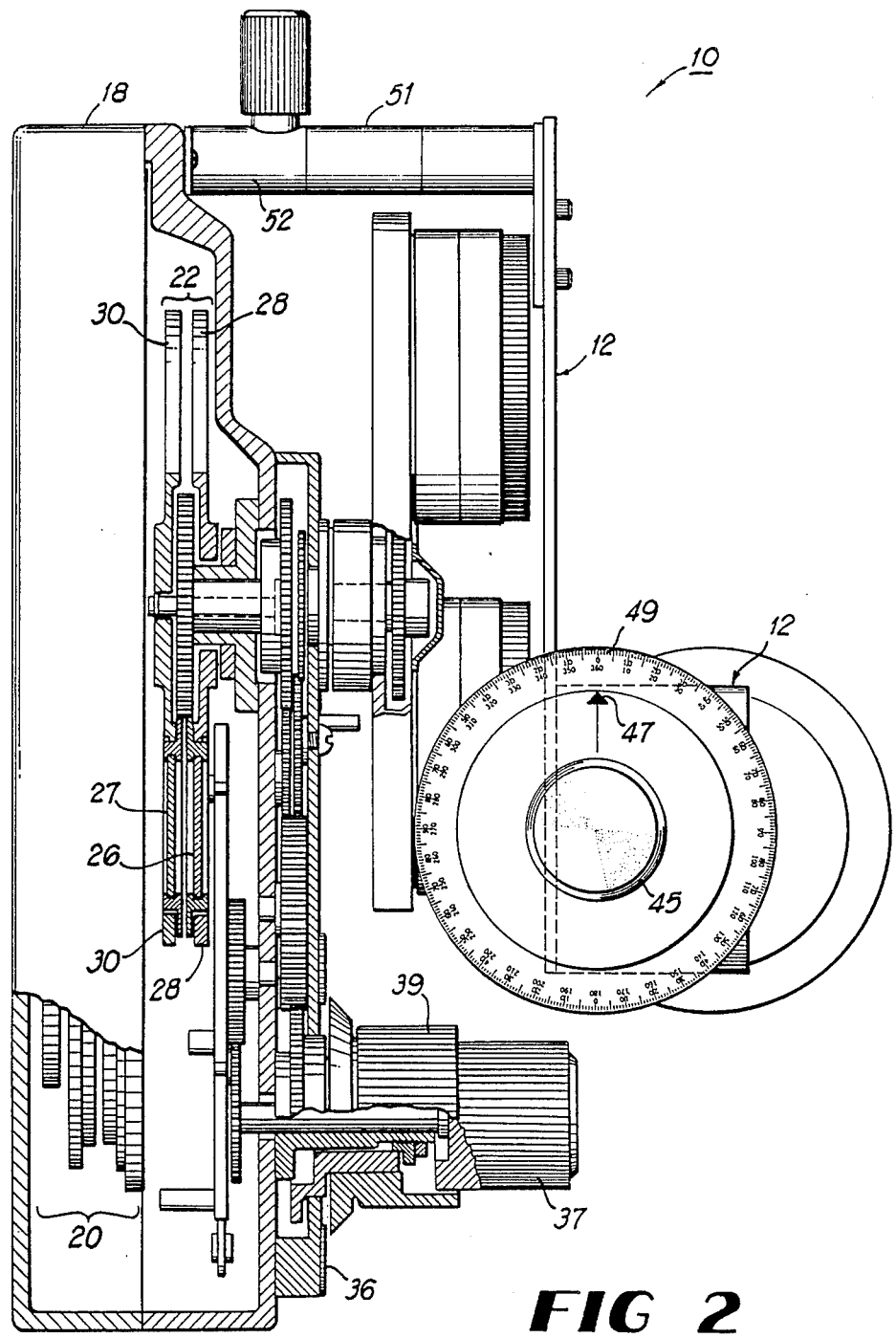
FIG. 2 is a cross-sectional view of the left eye battery taken substantially vertically through the viewing tube of the refractor, illustrating the selectable crossed cylinder assembly and the variable crossed cylinder assembly of FIG. 1.
Figure 3:
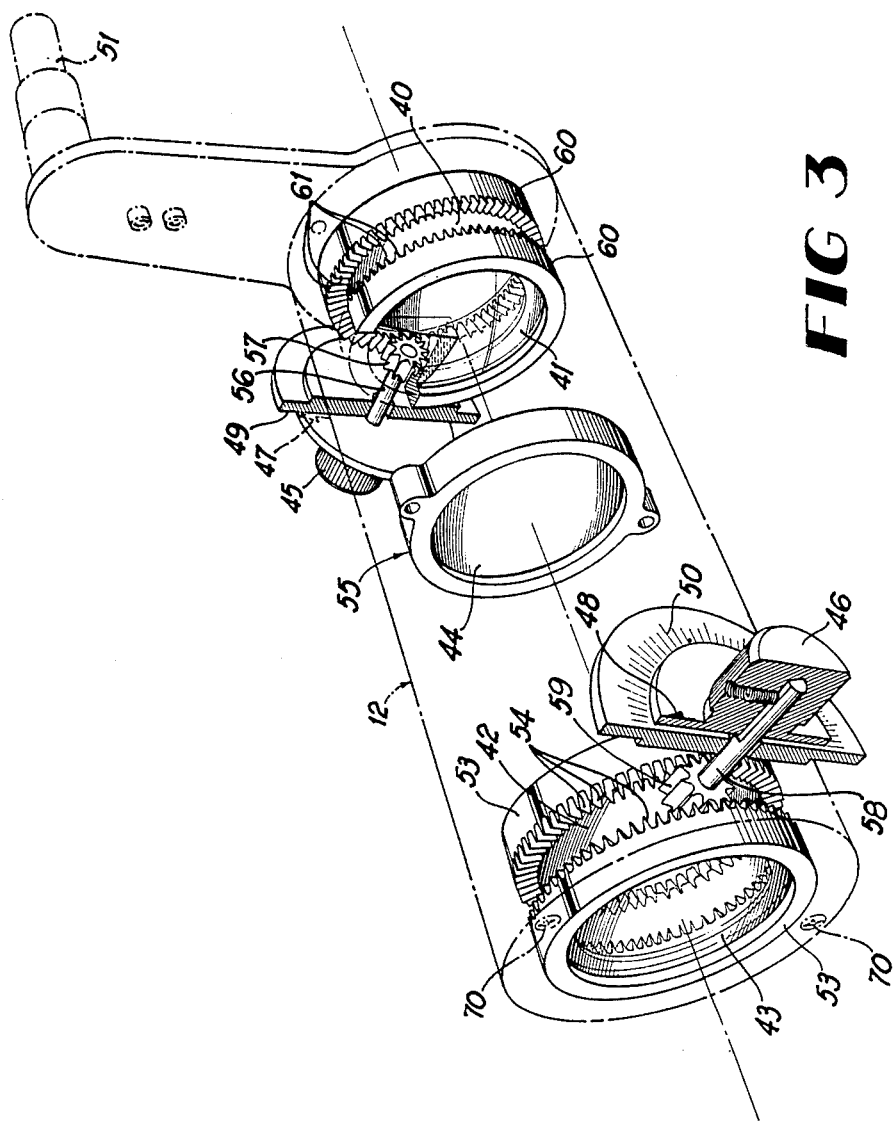
FIG. 3 is an exploded perspective view of the variable crossed cylinder assembly of FIG. 1.

The variable five-lens crossed cylinder assembly 12 of the present invention (FIGS. 1, 2, and 3) includes counter rotating lenses 40, 41, 42, and 43, and lens 44 which is stationary within assembly 12 (FIG. 3). Lenses 40, 41, 42, and 43 are cylinder lenses of equal power, each of which has a power equal to one-half of the power of stationary sphere lens 44 of opposite sign. For example, stationary lens 44 may be a +6.00 D sphere while rotating lenses 40, 41, 42, and 43 are each a −3.00 D cylinder. Likewise, the stationary lens 44 may be a +3.00 D sphere while rotating lenses 40, 41, 42, and 43 are each a −1.50 D cylinder.

Lenses 40 and 41 are operated by knob 45, while knob 46 operates lens 42 and 43. Lenses 40 and 41 are shown paired and positioned behind sphere lens 44 and lenses 42 and 43 are shown paired and positioned in front of lens 44. However, the ordering of lenses 40, 41, 42, 43, and 44 within the crossed cylinder assembly 12 is not critical to the operation of the present invention.

Referring to FIGS. 2 and 3, knob 45 contains shaft 56 with gear 57 located at the end and positioned between rings 60 containing lenses 40 and 41. Rings 60 contain grooves 61 which form gear teeth that mesh with teeth of gear 57 and are rotated by gear 57 when knob 45 is turned. As knob 45 is turned the two rotating lenses 40 and 41 will rotate in opposite directions to each other at an equal rate relative to a stationary combined lens axis. The combined lens axis always will bisect the angle formed by the axes of lenses 40 and 41. In a similar manner knob 46 contains shaft 58 with gear 59 located at the end and positioned between rings 53 containing lenses 42 and 43. Teeth of gear 59 engage the parallel grooves 54 of rings 53 when knob 46 is turned. As knob 46 is turned the two rotating lenses 42 and 43 will counter rotate at an equal rate relative to each other. Like the combined lens axis of lenses 40 and 41, the combined lens axis of lenses 42 and 43 always will bisect the angle formed by the axes of lenses 42 and 43.

Critical to the present invention is placement of the lens axes so that the combined lens axis of lenses 40 and 41 is offset 45 degrees from the combined lens axis of lenses 42 and 43. The resulting power of the assembly 12 will be indicated by the position of pointers 47 and 48 on scales 49 and 50 contained on knobs 45 and 46, respectively. The power of the combined lenses 40, 41, 42, 43, and 44 will be zero when the axes of 40 and 41 are 90 degrees to each other and the axes of 42 and 43 are 90 degrees to each other.

The assembly 12 is detachably mounted to the refractor 10, which may be either a standard sphere/cylinder phoropter or a crossed cylinder phoropter, so that lenses 40, 41, 42, 43, and 44 are aligned with refractor viewing tube 24 for the eye being refracted. As shown in FIGS. 1 and 2 assembly 12 contains a male member 51 which may be inserted into a female member 52 appropriately positioned on refractor 10. The two-battery refractor 10 of FIG. 1 shows two female members 52, one each for the right and left batteries 16 and 18. By using this, or any other, detachable mounting technique, a single assembly 12 may be moved back and forth between batteries 16 and 18. Likewise, a track can be mounted horizontally across the refractor 10 and a single assembly 12 slidably attached so that assembly 12 can be positioned either in front of batteries 16 or 18 or out of the optical path of both. Alternatively, assembly 12 could be connected to a microscope, telescope, or video camera in any appropriate manner so that lenses 40, 41, 42, 43, and 44 are aligned with the viewing tube of the device.

A substantially suitable structure for variable crossed cylinder lens attachment may be provided by mounting stationary lens 44 in loupe 55 (FIG. 3) and by substituting lenses 40 and 41 in place of the prisms normally used in a conventional Risley rotary prism loupe attachment. The modified Risley prism attachment may be mounted on loupe 55, which corresponds to loupe 158 of the Jackson crossed cylinder loupe assembly described in U.S. Pat. No. 3,498,699. Similarly, lenses 42 and 43 also may be mounted in a modified Risley rotary prism loupe attachment and mounted on loupe 55 of assembly 12. Set screws 70 extend through assembly 12 to hold loupe 55 and the two modified Risley prism attachments in place.

In one embodiment of my invention, position information for the variable lens assembly 12 may be input directly to a computer which is programmed to calculate and display the resulting power of the lenses in assembly 12. Such data can also be appropriately combined by the computer with any sphere lenses also utilized in the refractor to correct the patient's refractive error and with the patient's spectacle lens power, if over-refraction is being practiced, to display and print out the patient's final prescription.

Figure 4:
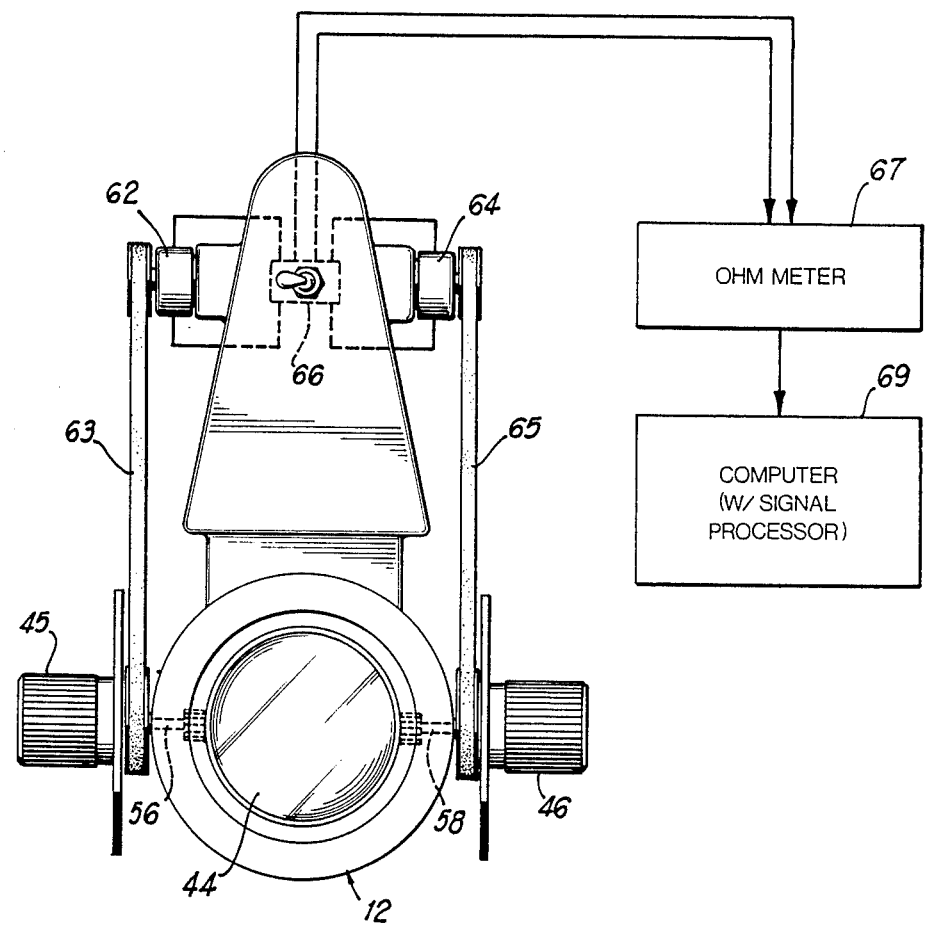
FIG. 4 is a diagram of an embodiment of the present invention including a front view of the variable crossed cylinder assembly and showing its connection to a computer and associated equipment.

For instance, as is illustrated in FIG. 4, a precision potentiometer 62 may be mechanically coupled via belt 63 to shaft 56 to sense the angular position of lenses 40 and 41. A similar potentiometer 64 may be coupled via belt 65 to shaft 58 for the same purpose with respect to lenses 42 and 43. Switch 66 is used to connect first one and then the other of potentiometers 62 and 64 to ohmmeter 67. The resistance values measured by ohmmeter 67 will be proportional to the angular displacements of the lenses of each pair of identical cylinder lenses from the corresponding combined lens axis and are input to a conventional computer 69 capable of processing the signals. The power of sphere lens 44 may be preprogrammed into the computer 69 so that it may compute the combined power of the crossed cylinder lens assembly (see FIG. 4). Likewise, a microprocessor could be connected directly to potentiometers 62 and 64 or other appropriate sensing means to compute the combined power of the crossed cylinder assembly.

The enhanced range of cylinder powers and axes possible utilizing the five-lens system of the assembly 12 described here, as compared to a pair of counter-rotating equal but opposite power cylinder lenses or the three-lens system as described in my previous applications, may be understood by comparison of the three type of lens systems. First a system containing equal but opposite cylinders in accordance with the teaching of my previous applications Ser. Nos. 06/670,398 and 07/023,980:

CHART 1

| | |
|---|---|
| Clockwise rotating lens | 0.00 −3.00 × 90 |
| Counterclockwise rotating lens | 0.00 +3.00 × 90 |

RESULTANT CROSSED CYLINDER AS GENERATED WITH ABOVE CYLINDERS FOR VARIOUS DEGREES OF ANGULAR COUNTER ROTATION OF EACH CYLINDER

| COUNTER ROTATION (Deg.) | RESULTANT CROSSED CYLINDERS |
|---|---|
| 1 | −0.10 +0.21 × 135° or 45° |
| 2 | −0.21 +0.42 × 135° or 45° |
| 5 | −0.52 +1.04 × 135° or 45° |
| 10 | −1.03 +2.05 × 135° or 45° |
| 15 | −1.50 +3.00 × 135° or 45° |
| 18 | −1.76 +3.53 × 135° or 45° |
| 21 | −2.01 +4.01 × 135° or 45° |
| 24 | −2.23 +4.46 × 135° or 45° |
| 28 | −2.49 +4.97 × 135° or 45° |
| 33 | −2.74 +5.48 × 135° or 45° |
| 45 | −3.00 +6.00 × 135° or 45° |

Next the three-lens system of may previous application Ser. No. 07/116,322:

CHART 2

| | |
|---|---|
| Stationary lens | 0.00 −3.00 × 180° |
| Rotatable lens | 0.00 +1.50 × 180° |
| Rotatable lens | 0.00 +1.50 × 180° |

RESULTANT CROSSED CYLINDER POWER AS GENERATED WITH COUNTER ROTATION OF THE +1.50 CYLINDERS AND STATIONARY −3.00 CYLINDER

| COUNTER ROTATION (Deg.) | RESULTANT CROSSED CYLINDER |
|---|---|
| 17 | −0.25 +0.51 × 90° |
| 21 | −0.38 +0.77 × 90° |
| 24 | −0.49 +0.99 × 90° |
| 27 | −0.62 +1.24 × 90° |
| 30 | −0.75 +1.50 × 90° |
| 33 | −0.89 +1.78 × 90° |
| 35 | −0.98 +1.97 × 90° |
| 38 | −1.13 +2.27 × 90° |
| 40 | −1.24 +2.48 × 90° |
| 43 | −1.39 +2.79 × 90° |
| 45 | −1.50 +3.00 × 90° |
| 50 | −1.76 +3.52 × 90° |
| 55 | −2.01 +4.03 × 90° |
| 60 | −2.25 +4.50 × 90° |
| 75 | −2.46 +4.93 × 90° |
| 84 | −2.77 +5.54 × 90° |

CHART 2-continued

| | |
|---|---|
| Stationary lens | 0.00 −3.00 × 180° |
| Rotatable lens | 0.00 +1.50 × 180° |
| Rotatable lens | 0.00 +1.50 × 180° |

RESULTANT CROSSED CYLINDER POWER AS GENERATED WITH COUNTER ROTATION OF THE +1.50 CYLINDERS AND STATIONARY −3.00 CYLINDER

| COUNTER ROTATION (Deg.) | RESULTANT CROSSED CYLINDER |
|---|---|
| 90 | −3.00 +6.00 × 90° |

Finally, for the system of the present invention:

CHART 3

| | |
|---|---|
| Stationary lens | +6.00 |
| Counterrotatable lens pair A: | |
| Rotatable lens | 0.00 −3.00 × 180° |
| Rotatable lens | 0.00 −3.00 × 180° |
| Counterrotatable lens pair B: | |
| Rotatable lens | 0.00 −3.00 × 45° |
| Rotatable lens | 0.00 −3.00 × 45° |

RESULTANT CROSSED CYLINDER POWER AS GENERATED WITH BOTH PAIRS OF COUNTERROTATABLE LENSES AND THE STATIONARY LENS FOR VARIOUS DEGREES OF ANGULAR POSITION

| COUNTER ROTATION PAIR A (Deg.) | COUNTER ROTATION PAIR B (Deg.) | RESULTANT CROSSED CYLINDER POWER FOR PAIR A, PAIR B AND THE STATIONARY LENS |
|---|---|---|
| 0 | 0 | 0.00 0.00 |
| 10 | 10 | −0.15 +0.30 × 23° |
| 20 | 10 | −0.23 +0.47 × 13° |
| 40 | 20 | −0.47 +0.93 × 13° |
| 60 | 10 | −0.63 +1.27 × 5° |
| 80 | 20 | −0.85 +1.71 × 7° |
| 300 | 10 | −2.60 +5.71 × 1° |
| 10 | −10 | −0.15 +0.30 × 157° |
| 10 | −140 | −1.41 +2.82 × 137° |
| 20 | −10 | −0.23 +0.47 × 167° |
| 80 | −10 | −0.83 +1.67 × 176° |
| 180 | −20 | −1.78 +3.55 × 177° |
| 330 | −140 | −3.08 +6.16 × 166° |
| −10 | 10 | −0.15 +0.30 × 67° |
| −20 | 10 | −0.23 +0.47 × 77° |
| −40 | 20 | −0.47 +0.93 × 77° |
| −60 | 10 | −0.63 +1.25 × 85° |
| −80 | 20 | −0.83 +1.67 × 86° |
| −300 | 10 | −2.60 +5.20 × 89° |
| −10 | −10 | −0.15 +0.30 × 113° |
| −10 | −140 | −1.41 +2.82 × 133° |
| −20 | −10 | −0.23 +0.47 × 103° |
| −80 | −10 | −0.83 +1.67 × 94° |
| −180 | −20 | −1.78 +3.55 × 93° |
| −330 | −140 | −3.08 +6.16 × 104° |

As can be seen from Chart 3, a relatively modest cylinder power change may result for a given rotation of the lenses, particularly at the lower end of the range of powers. Because the refractive errors of the eyes of most patients are not large, the present system allows for a more accurate determination of the amount of the correction needed. Additionally, the angle of the resultant cylinder component of the lens system is continuously variable by rotation of the two pairs of lenses. Each of Pairs A and B may be manipulated independently, so that a wide range of sphere and cylinder powers may be obtained throughout the entire range of resulting angular positions.

Additional understanding of the present invention may be achieved by comparing its operation to that of the device described in U.S. Pat. No. 3,822,932 to Humphrey, which patent is incorporated herein in its entirety by this reference. Humphrey discloses a system (Snellen-Stokes) comprising two pairs of counter rotating cylinder lenses, with the combined lens axis of one pair offset 45 degrees from the combined lens axis of the other. The lenses within each pair are of equal and opposite power, so that when the axes of the two lenses are parallel the resultant power for the pair will be zero. Moreover, in Humphrey's design the resultant cylinder power for each pair increases to its maximum level as the lenses are rotated 45 degrees from the parallel axes position.

By contrast, the present invention results in maximum power occurring when the axes of the two cylinder lenses are parallel and the resultant power decreases to zero as the axes of the cylinder lenses are rotated 45 degrees from the parallel position. Resultant crossed cylinder powers for the present invention are 45 degrees out of phase from those achieved in Humphrey's design. Chart 4 details the difference between the resultant powers as the cylinders are counter-rotated 90 in the two designs.

CHART 4

| | | |
|---|---|---|
| Sims' Lens: | Cylinder 1 ($-3.00 \times 180°$) and Cylinder 2 ($-3.00 \times 180°$) are counter-rotated relative to sphere $+3.00$ D | |
| Snellen-Stokes' Lens: | Cylinder 1 ($-3.00 \times 180°$) and Cylinder 2 ($+3.00 \times 180°$) are counter-rotated relative to each other | |
| Conclusion: | The generated crossed cylinders of the two different lens systems are 45° out of phase to each other. | |

| COUNTER ROTATION (Degrees) | SIMS' LENS | SNELLEN-STOKES' LENS |
|---|---|---|
| 0° | $+3.00 -6.00 \times 180°$ | $0.00\ 0.00 \times 000$ |
| 45° | $0.00\ 0.00 \times 000$ | $-3.00 +6.00 \times 45°$ (or 135°) |
| 90° | $+3.00 -6.00 \times 90°$ | $0.00\ 0.00 \times 000$ |

OPERATION

A refractor modified in accordance with the present invention may be used to refract a patient's eye by first using the spherical lens in sphere lens assembly 20 to produce a fog. With the patient either wearing or not wearing his glasses and observing the smallest discernible visual acuity line, this fog is then reduced in 0.25 D steps in order to determine the spherical equivalent. The typical patient responses to such fog reduction would be: blurred—clear—sharper and darker. The "blurred" response would typically represent a 0.50 D fog, the "clear" response a 0.25 D fog and the "sharper and darker" response the spherical equivalent meridional balance.

The variable crossed cylinder lens assembly 12 is then positioned in alignment with the viewing tube 24 for the eye being refracted. Initially the knobs 45 and 46 should be turned so that the axis of each lens of a pair is 90 degrees to the axis of its corresponding lens. In such a position the resultant crossed cylinder lens power is 0.00 D. The patient is then asked to rotate knobs 45 and 46 independently and alternatively until the best visual acuity is obtained. As the visual acuity of the eye being examined is improved, the visual acuity line on which the patient is asked to focus is reduced in size, and the positions of knobs 45 and 46 are adjusted slightly, if necessary, to obtain the best image much as one might fine tune a radio receiver. This process is repeated until maximum visual acuity for the eye under test is achieved. Similarly, if assembly 12 is connected to a microscope, telescope, video camera, or other similar device that provides only spherical adjustment, the user can manipulate the controls on the device to obtain the best sphere and then rotate knobs 45 and 46 as discussed above to neutralize any cylindrical error.

The resulting astigmatic correction may be confirmed by using the selectable crossed cylinder lens assembly to place an additional $-0.25+0.50$ D crossed cylinder lens at various angles (0, 45, 90, and 135 degrees) in the optical path and noting the patient's response. Likewise, if assembly 12 is used with Jackson crossed cylinders in a convention phoropter, sphere and cylinder lenses equivalent to the resultant power and angle obtained by manipulating the variable assembly 12 may be rotated into the optical path and the Jackson crossed cylinders used to confirm the results.

My invention is not limited to the embodiments described and represented above, and various modifications can be made thereto without departing from the scope and spirit of the preceding description and the following claims.

I claim:

1. A refractor comprising at least one variable crossed cylinder lens assembly comprising:
   a. a sphere lens;
   b. a first pair of identical cylinder lenses, each of which cylinder lens is of power equal to one-half the power of the sphere lens and of opposite sign, mounted in a means for rotating each cylinder lens in the direction opposite the other at the same rate relative to a first combined lens axis; and
   c. a second pair of identical cylinder lenses, each of which cylinder lens is of power equal to one-half the power of the sphere lens and of opposite sign, mounted in a means for rotating each cylinder lens in the direction opposite the other at the same rate relative to a second combined lens axis, which axis is offset 45 degrees from the first combined lens axis.

2. A refractor comprising:
   a. at least one battery comprising:
      i. a viewing tube; and
      ii. a selectable sphere lens assembly; and
   b. at least one variable crossed cylinder lens assembly comprising:
      i. a sphere lens;
      ii. a first pair of identical cylinder lenses, each of which cylinder lens is of power equal to one-half the power of the sphere lens and of opposite sign, mounted in a means for rotating each cylinder lens in the direction opposite the other at the same rate relative to a first combined lens axis; and
      iii. a second pair of identical cylinder lenses, each of which cylinder lens is of power equal to one-half the power of the sphere lens and of opposite sign, mounted in a means for rotating each cylinder lens in the direction opposite the other at the same rate relative to a second combined lens axis, which axis is offset 45 degrees from the first combined lens axis.

3. A refractor according to claim 2 in which the battery further comprises a selectable crossed cylinder lens assembly.

4. A refractor according to claim 2 further comprising a means for mounting the variable crossed cylinder lens assembly to the battery so that the assembly may be positioned in alignment with the viewing tube of the battery.

5. A refractor according to claim 2 in which the selectable sphere lens assembly comprises:
   a. at least one lens-carrying disc carrying a plurality of graded sphere lenses; and
   b. means for rotating the disc whereby any selected one sphere lens in the disc may be positioned in alignment with the viewing tube.

6. A refractor according to claim 3 in which the selectable crossed cylinder lens assembly comprises:
   a. at least one lens-carrying crossed cylinder disc carrying a plurality of graded crossed cylinder lenses;
   b. means for rotating the disc whereby any selected one crossed cylinder lens in the disc may be positioned in alignment with the viewing tube; and
   c. means for rotating the selected crossed cylinder lens positioned in alignment with the viewing tube.

7. A refractor according to claim 2 further comprising:
   a. means for sensing the angular displacement of the lens axes of each pair of identical cylinder lenses from its corresponding combined lens axis; and
   b. means for computing from the sensed angular displacement information the combined power of the sphere lens and the first and second pairs of identical cylinder lenses of the variable crossed cylinder lens assembly.

8. A refractor according to claim 7 in which the sensing means comprises a potentiometer coupled to each means for rotating each cylinder lens of a pair of identical cylinder lenses.

9. A refractor according to claim 7 in which the computing means comprises a computer.

10. A refractor comprising:
    a. at least one battery comprising:
       i. a viewing tube; and
       ii. a selectable crossed cylinder lens assembly; and
    b. at least one variable crossed cylinder lens assembly comprising:
       i. a sphere lens;
       ii. a first pair of identical cylinder lenses, each of which cylinder lens is of power equal to one-half the power of the sphere lens and of opposite sign, mounted in a means for rotating each cylinder lens in the direction opposite the other at the same rate relative to a first combined lens axis; and
       iii. a second pair of identical cylinder lenses, each of which cylinder lens is of power equal to one-half the power of the sphere lens and of opposite sign, mounted in a means for rotating each cylinder lens in the direction opposite the other at the same rate relative to a second combined lens axis, which axis is offset 45 degrees from the first combined lens axis.

11. A refractor according to claim 10 further comprising a means for mounting the variable crossed cylinder lens assembly to the battery so that the assembly may be positioned in alignment with the viewing tube of the battery.

12. A refractor according to claim 10 in which the selectable crossed cylinder lens assembly comprises:
    a. at least one lens-carrying crossed cylinder disc, carrying a plurality of graded crossed cylinder lenses;
    b. means for rotating the disc whereby any selected one crossed cylinder lens in the disc may be positioned in alignment with the viewing tube; and
    c. means for rotating the selected crossed cylinder lens positioned in alignment with the viewing tube.

13. A refractor according to claim 10 further comprising:
    a. means for sensing the angular displacement of the lens axes of each pair of identical cylinder lenses from its corresponding combined lens axis; and
    b. means for computing from the sensed angular displacement information the combined power of the sphere lens and the first and second pairs of identical cylinder lenses of the variable crossed cylinder lens assembly.

14. A refractor according to claim 13 in which the sensing means comprises a potentiometer coupled to each means for rotating each cylinder lens of a pair of identical cylinder lenses.

15. A refractor according to claim 13 in which the computing means comprises a computer.

16. A refractor comprising:
    a. at least one battery comprising:
       i. a viewing tube;
       ii. a selectable sphere lens assembly comprising:
          A. at least one lens-carrying disc carrying a plurality of graded sphere lenses; and
          B. means for rotating the disc whereby any selected one sphere lens in the disc may be positioned in alignment with the viewing tube; and
       iii. a selectable crossed cylinder lens assembly comprising:
          A. at least one lens-carrying crossed cylinder disc carrying a plurality of graded crossed cylinder lenses;
          B. means for rotating the disc whereby any selected one crossed cylinder lens in the disc may be positioned in alignment with the viewing tube; and
          C. means for rotating the selected crossed cylinder lens positioned in alignment with the viewing tube; and
    b. at least one variable crossed cylinder lens assembly comprising:
       i. a sphere lens;
       ii. a first pair of identical cylinder lenses, each of which cylinder lens is of power equal to one-half the power of the sphere lens and of opposite sign, mounted in a means for rotating each cylinder lens in the direction opposite the other at the same rate relative to a first combined lens axis;
       iii. a second pair of identical cylinder lenses, each of which cylinder lens is of power equal to one-half the power of the sphere lens and of opposite sign, mounted in a means for rotating each cylinder lens in the direction opposite the other at the same rate relative to a second combined lens axis, which axis is offset 45 degrees from the first combined lens axis; and
       iv. means for mounting the variable crossed cylinder lens assembly to the battery so that the assembly may be positioned in alignment with the viewing tube of the battery.

17. A refractor according to claim 16 further comprising:
    a. means for sensing the angular displacement of the lens axes of each pair of identical cylinder lenses from its corresponding combined lens axis; and b. means for computing from the sensed angular displacement information the combined power of the sphere lens and the first and second pairs of identical cylinder lenses of the variable crossed cylinder lens assembly.

18. A refractor according to claim 17 in which the sensing means comprises a potentiometer coupled to each means for rotating each cylinder lens of a pair of identical cylinder lenses.

19. A refractor according to claim 17 in which the computing means comprises a computer.

20. A method of refracting an eye of a patient using a refractor comprising the steps of:
   a. determining the spherical component of the refractive error of the eye and placing a sphere lens of power appropriate to correct such spherical refractive error in the optical path of the eye;
   b. placing in the optical path of the eye a variable crossed cylinder lens assembly comprising a sphere lens, a first pair of identical cylinder lenses having a first combined lens axis, and a second pair of identical cylinder lenses having a second combined lens axis, which axis is offset 45 degrees from the first combined lens axis;
   c. counter rotating the two lenses in the first pair of identical cylinder lenses and noting the patient's response thereto;
   d. counter rotating the two lenses in the second pair of identical cylinder lenses and noting the patient's response thereto; and
   e. repeating steps (c) and (d) until optimal correction of the refractive error of the eye is achieved.

21. A refractor comprising:
   a. at least one variable crossed cylinder lens assembly comprising at least one pair of cylinder lenses mounted in a means for rotating each cylinder lens in the direction opposite the other at the same rate relative to a combined lens axis;
   b. means for sensing the angular displacement of the lens axes from the combined lens axis and generating at least one signal proportional thereto; and
   c. a computer for receiving the signal and computing therefrom the combined lens power of the variable crossed cylinder lens assembly.

* * * * *